United States Patent [19]

Van Gompel

[11] Patent Number: 4,630,320
[45] Date of Patent: Dec. 23, 1986

[54] GARMENT WITH ONE OR MORE GUSSETED ADJUSTABLE OPENINGS AND METHOD OF MAKING THE SAME

[75] Inventor: Paul T. Van Gompel, Hortonville, Wis.

[73] Assignee: Kimberly-Clark Corporation, Neenah, Wis.

[21] Appl. No.: 789,205

[22] Filed: Oct. 18, 1985

[51] Int. Cl.⁴ .............................. A43B 1/22; A41B 9/04
[52] U.S. Cl. ............................................. 2/406; 2/183; 2/197; 2/68; 2/237
[58] Field of Search .................... 2/407, 406, 403, 404, 2/400, 183, 202, 197, 68, DIG. 11, 237, 243 R

[56] References Cited

U.S. PATENT DOCUMENTS

| | | | |
|---|---|---|---|
| 1,716,065 | 6/1929 | Kiamie . | |
| 2,856,608 | 10/1958 | Wagenfeld | 2/183 X |
| 3,150,665 | 9/1964 | May, Jr. et al. | 128/288 |
| 3,945,051 | 3/1976 | Burkard | 2/224 |
| 3,988,568 | 10/1976 | Mantell | 2/183 X |
| 4,145,763 | 3/1979 | Abrams et al. | 2/403 |
| 4,468,815 | 9/1984 | Pellegri | 2/68 |

FOREIGN PATENT DOCUMENTS 543369  2/1942  United Kingdom ..................... 2/224

Primary Examiner—H. Hampton Hunter
Attorney, Agent, or Firm—Douglas L. Miller; Donald L. Traut

[57] ABSTRACT

A garment, such as an incontinence control garment, having an opening to accommodate a part of the wearer's body, such as a leg opening, includes one or more gusset folds at the opening and having at least a portion of the faces of the gusset fold, e.g., the lateral edges thereof, manually disengagably bonded to one another, whereby the opening may be increased in size by manual disengagement of the bonded outer lateral edges. For example, a disposable panty-type garment having leg openings which are manually adjustable in size is provided, each featuring the disengagably bonded gusset fold structure described above. Also disclosed is a method for making garments such as panty-type garments, by the steps which may include cutting articles from a web of material, longitudinally folding the sheet to form a garment having closed leg openings, and folding the material at the opening to form gusset folds thereat which may be selectively opened to provide larger sized openings.

26 Claims, 5 Drawing Figures

GARMENT WITH ONE OR MORE GUSSETED ADJUSTABLE OPENINGS AND METHOD OF MAKING THE SAME

BACKGROUND OF THE INVENTION

1. Field of the Invention

This invention generally relates to garments made of flexible material such as nonwoven fabrics, and particularly to garments of such type which are adjustable to fit variously sized wearers, such as disposable diapers, panties, swimwear, rainwear, laboratory coats, paint smocks, and the like.

2. Description of the Prior Art

In the art of disposable clothing, such as for example garments of the general type referred to hereinabove, the fact that such garments are intended only for one or a limited number of uses prior to disposal requires that they be formed of low cost materials, such as paper, nonwoven synthetic fabrics, etc. Similarly, such articles are desirably manufactured in as inexpensive a manner as is feasible, consistent with their disposable character. However, the fact that such articles are intended to have but a limited useful life and typically are made of inexpensive materials by high speed manufacturing techniques, leads to problems of obtaining good fit for the wearer. For disposable articles such as paper laboratory overcoats, paint smocks and the like, this may not be a severe problem where such articles can be made somewhat oversized relative to the wearer's size and can readily be rolled up or cut for use as desired, even though expedients may be inconvenient. However, disposable garments such as short pants, diapers, training panties and the like have more demanding fit requirements in that they must be reasonably comfortable and conformable to the wearer without necessity of undue modification of the garment by the user/wearer. One approach that has been employed with such garments is the use of elastic waist and leg gathers which, within a given range of sizes, provide a conformable fit to wearers of different waist, leg, etc., sizes. Nonetheless, for the purpose of high speed, low cost production, the use of elastic strips, e.g., spandex bands, tensioned elastomeric tapes and the like, have the disadvantages that such means introduce an additional oomplexity into the manufacturing process and increase the manufacturing cost of the garment. Accordingly, it would be an advance in the art to provide a garment having an opening through which an extremity or other part of the wearer's body is insertable, wherein the garment opening is able to accommodate a variety of sizes and which is easily manufactured at low cost.

U.S. Pat. No. 1,716,065 to N. A. Kiami discloses a diaper adapted for adjustment of the sizes of the waist opening as well as the leg openings. The diaper has on its transverse and end margins a series of spaced-apart buttonholes accommodating button fasteners which may be inserted into various buttonholes along the respective edges to adjust the size of the waist and leg openings.

U.S. Pat. No. 3,150,665 to W. L. May, Jr., et al discloses a waterproof panty of heat sealable plastic material which is cut or stamped from a single sheet to form front and rear portions connected by a narrower crotch portion and adapted to define leg openings of the panty when side edges of the front and rear sheet portions are secured together along side seams. A binding, or trim, is provided around the waist opening of the panty and similar bindings are secured around the leg openings. In this disclosed article, the front and rear portions each are folded inwardly along their edges at the side seams in the form of inwardly extending flanges. The flanges are superimposed on each other at the seams and held together by plural heat seals spaced apart from one another along the length of the flanges. The flanges contact one another along the heat sealed portions and separate slightly from one another between the heat seals to form ventilation openings for the panty.

U.S. Pat. No. 3,945,051 to E. R. Burkard discloses short pants in which left and right seat panels are independent of left and right front panels, with the seat panels being attached to the waistband at their upper edges and extending over substantially greater than one-half of the circumferential direction of the waistband. The forward edges of the seat panels slant downwardly and rearwardly from the waistband so that the front panels overlap the left and right seat panels at the waistband. The garment disclosed in this patent involves the use of overlapping front and rear panels which are not bonded to one another in any way, so that the garment accommodates movement of the wearer, with the front overlapped panel moving with the leg of the wearer in the forward or lateral direction relative to the rear panel.

U.S. Pat. No. 4,145,763 to J. L. Abrams, et al discloses a surgical/medical undergarment comprising at least two completely separable cloth panels which are removably fastened to one another by the use of Velcro ® fasteners or similar adhering materials. The disclosed undergarment may also contain a slit positioned near the urinary tract for catheterization or drainage, and/or adhering means for keeping a folded-back upper or lower side or crotch portion of the undergarment open and secured in place during examination, treatment or surgery. Both the slit and the adhering means are also separably sealed by Velcro ® fasteners or similar adhering material.

British Patent Specification No. 543,369 to H. Perry discloses knickers composed of two pieces of fabric each substantially rectangular and each having at one side edge a substantially triangular extension. The lower edge of the triangular extension extends down to the bottom corners of the piece and the upper edge thereof merges upwardly with a concave curve into the side edge of the piece. Each of the pieces is folded to bring the aforementioned lower edge into register with the lower part of the other side edge of the piece. The meeting edges are seamed together to provide the leg portion with a seam at the inside thereof, the two pieces also being seamed together with a central rear seam joining the upper edges of the extensions and the side edges into which they merge. The rear seam extends forward beneath the crotch to the leg seams. A central front seam joins the other side edges of the two pieces above the part of the edges that is seamed by the leg seam to the lower edge of the extension.

None of the foregoing approaches taught by prior art is wholly satisfactory for providing adjustably sizable extremity openings, particularly in disposable garments in a readily manufactured manner at low cost, particularly with reference to undergarments such as disposable panty-type garments, as is provided by the present invention.

SUMMARY OF THE INVENTION

In accordance with the present invention there is provided a garment including at least one opening for encircling a portion of the wearer's body and having at the periphery of the opening a gusset fold comprised of disengagably bonded together gusset faces, which optionally may be intermittently bonded together, whereby the opening can be increased in size by manual disengagement of at least a portion of the bonded together gusset faces.

In another aspect of the invention, the bonded together faces of the gusset fold are inwardly-folded sections of an outer-facing surface of the garment and define a lateral gusset seam in said outer-facing surface.

Another aspect of the invention provides that the gusset faces are disengagably bonded together along the lateral gusset seam, and optionally are intermittently disengagably bonded together along the lateral seam.

Yet another aspect of the invention provides that the bonded together faces of the gusset fold are sections of an inner-facing surface of the garment, whereby the gusset fold is disposed exteriorly of the opening.

Other aspects of the invention provide one or more of the following features: the gusset fold may be folded along a central fold line and may comprise two disengagably bonded together faces; the central fold line may coincide with a seam of the garment; the central fold line may be reinforced against tearing; at least the gusset fold of the garment may comprise a thermally bondable material and the gusset faces are thermally disengagably bonded together, e.g., ultrasonically bonded together; and the garment may comprise gusset folds at the leg openings, each converging in a direction away from an associated leg opening and with outer lateral edges thereof being manually disengagably bonded to one another, whereby the leg openings may be adjusted in use to larger sized legs, by manual disengagement of the bonded outer lateral edges of the gussets.

In another aspect of the invention, the thermally bondable material is weakened in the area immediately adjacent the disengagably bonded areas to facilitate disengagement of the bonded together gusset faces by mechanical failure of the material in the weakened area.

In accordance with the method aspects of the present invention, there is provided a method for making a garment having adjustable openings therein for encircling a portion of a wearer's body, the method comprising the steps of: providing a garment having one or more of said openings therein; folding, e.g., inwardly angularly folding, material at said openings to form therein gusset faces providing one or more gusset folds at the edge of said leg openings; and manually disengagably bonding, e.g., intermittently disengagably bonding, gusset faces of the gusset folds to one another.

Other method aspects include forming gusset seams and folding material in a manner to provide the structures described above, including providing a panty-type garment by the steps of: providing a longitudinally-extending sheet of flexible material having arcuate cut-outs at its ends; longitudinally folding said sheet so that at each of said ends, transverse edges on either side of said arcuate cut-outs are superposed to form closed leg openings from said arcuate cut-outs; bonding said superposed transverse edges to form side seams, and bonding by thermally, e.g., ultrasonically, bonding the material.

Other aspects of the invention may be discerned from the following description of preferred embodiments of the invention.

DETAILED DESCRIPTION OF THE PREFERRED EMBODIMENTS

The garment of the present invention embodies a construction for manually adjusting the size of one or more openings therein which encircle the wearer's body, and which is simple in construction whereby the manufacture of such garment may readily be effected at low cost by high speed construction from continuous traveling webs of material.

As used herein, the term "opening" in the garment refers to any opening in the garment which accommodates any part of the wearer's body by encircling it, e.g., it refers to and includes arm, leg, waist and neck openings. Thus, although the invention will be hereinafter described in detail with specific reference to panty-type garments wherein the manually adjustable openings are leg openings, it will be appreciated that the present invention embraces manually adjustable collar openings, sleeves, waistbands, and the like. Thus, the invention encompasses openings for parts of the wearer's body in various garments including pants, panties shirts, smocks, trunks, socks, shoes, shoe covers, etc. The opening of the garment may be one which is not openable and closeable or otherwise adjustable in size, except for the gusset folds provided by the present invention. That is, the opening may be a fixed size opening except for the gusset folds.

Figure 1:
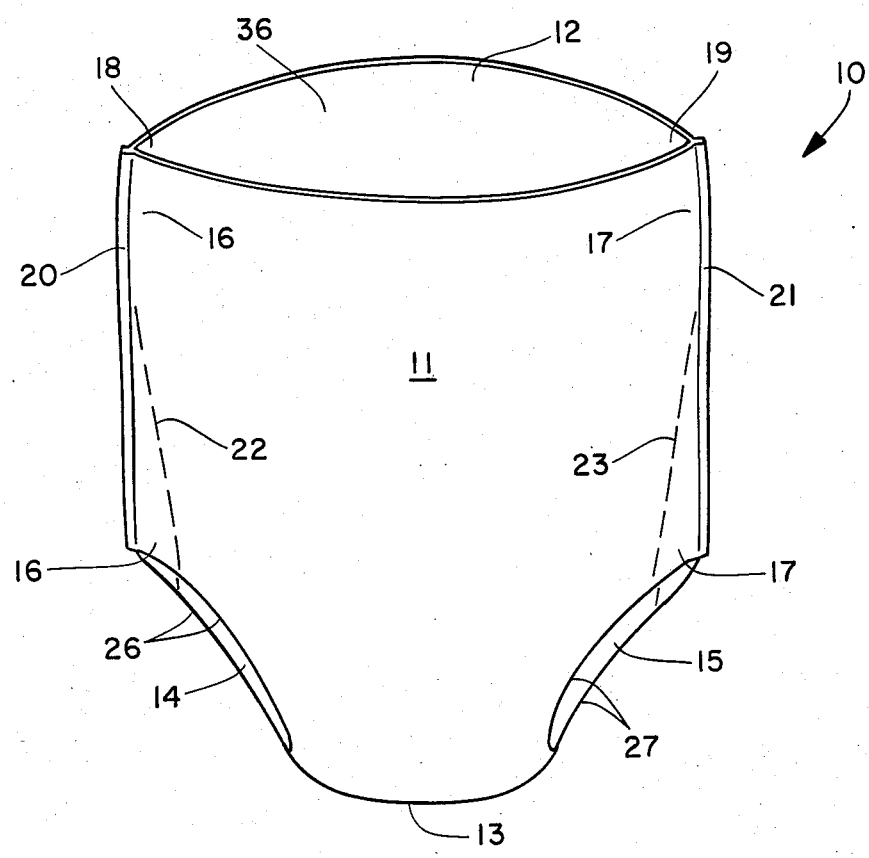
FIG. 1 is a perspective view of a panty-type garment having bonded side seams and configured to have gusset folds formed therein in the area shown in dotted line representation.

Referring now to FIG. 1, there is shown a perspective view of a panty-type garment 10 having a front panel 11 and a rear panel 12 integrally joined to one another at crotch section 13. On either side of the crotch section are leg openings 14, 15 bounded by respective leg opening edges 26 and 27. Front panel 11 is superposed on rear panel 12 in a manner more fully described below, such that respective front panel side margins 16, 17 are in register with the corresponding back panel side margins 18, 19, with the registered side margins 16, 18 bonded to one another by a continuous side seam 20, and the registered side margins 17, 19 bonded to one another by a continuous side seam 21.

The front and rear panels 11 and 12 of the garment with the integrally joining crotch section 13 constitute an assembly which may be cut from a unitary web or a plurality of overlaid unitary webs, in a manner which is well known, for example, in the manufacture of disposable diapers and the like. In such manufacturing techniques, pads of an absorbent material cut from a continuous moving web of the same, are sandwiched between a continuous moving web of a liquid-impervious backing sheet and a liquid-permeable front or liner sheet, and discrete, garments are cut from the joined webs. The garment may be formed of any suitable material or combinations of materials, such as, for example, nonwoven fabrics, thermoplastic sheets, etc. Typically, a training panty or incontinence control garment may be made from an outer, liquid-impervious material such as a polyolefin sheet, an inner liquid-pervious material such as a nonwoven web of polyolefin fibers and an intermediate, liquid absorbing sheet or pad sandwiched between the inner and outer liners. A particularly preferred material of construction for the garment of the type shown in FIG. 1 is a nonwoven sheet of polyolefin fiber material, such as a sheet of spunbonded or meltblown polyolefin fibers, which may be coated with a thermoplastic film to provide a liquid-impervious outer sheet as a composite material. In such construction, the thermoplastic film-coated side is used on the inside of the garment, and a second nonwoven sheet of material is used as the liquid-pervious liner. Such nonwoven and thermoplastic film materials are readily manufactured at low unit cost in high speed assembly operations. Thus, although not specifically shown in FIG. 1, the garment 10 may have disposed in the interior thereof a suitable absorbent pad or sheet or a multilayer absorbent material, e.g., a cellulosic nonwoven liner overlying a layer of air-felt or cotton batt material, covered by a liquid-pervious inner liner. Such construction provides a garment which may be used as a disposable training panty for infants or toddlers being toilet trained, or a disposable garment for incontinent persons of any age.

The side seams 20, 21 of the garment shown in FIG. 1 may be formed by any suitable manufacturing method conventionally employed for the specific material of construction. For materials such as spunbonded polypropylene fiber nonwoven webs or other thermoplastic films or nonwoven fabrics, the side seams may be formed by thermal bonding such as with a hot knife applied to the superposed margins or by a heated embossing roll, or by ultrasonic bonding techniques using an ultrasonic horn and a suitably shaped anvil to form the seam. In any event, the side seams preferably are continuous in character to provide uninterrupted joinder and reinforcement at the seams 20, 21 of the garment.

Subsequent to the forming of side seams 20 and 21, any side margins of material protruding outwardly from the seams may be severed from the formed garment. Alternatively, the seams may be formed with protruding side margins turned inwardly prior to forming the side seams 20 and 21. It is possible in some instances to bond side seams like seams 20 or 21 at the edge of the material without side margins of material protruding beyond the seams, thereby requiring no trimming or inward folding of protruding margins. However, the practice of high volume manufacture of garments from continuous webs of material travelling at high speeds, e.g., 300 to 500 feet per minute, generally requires a protruding side margin at the seams in order to give some latitude in the bonding area to insure good structural integrity of the seams in the mass-produced items.

The leg openings 14 and 15 on either side of the crotch section 13 are bounded by leg opening edges 26 and 27, which may, if desired, be provided with flexible gathers or other resilient tensioned material which enhance the fit of the garment. However, it is a specific feature of the present invention that adequate fit may be usefully provided without the use of such elasticity means, thereby simplifying the manufacturing process and reducing the cost of the garments. The dotted-lines 22 and 23 in FIG. 1 denote fold lines which will define, respectively, one of the outer lateral edges of gusset folds to be formed in the article, as described more fully hereinafter.

Figure 2:
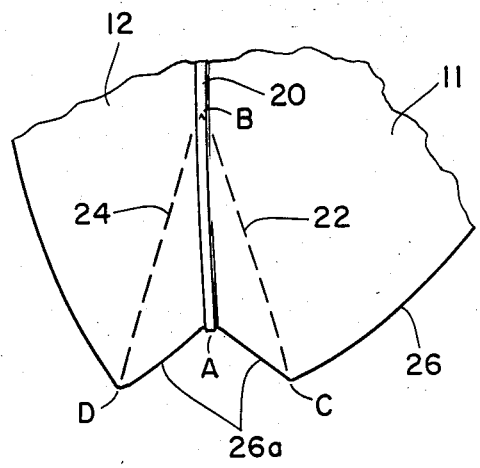
FIG. 2 is a perspective view of a portion of the FIG. 1 garment viewed at the side seam portion thereof, and showing an intermediate step in the forming of an inwardly folded gusset fold.

FIG. 2 shows a perspective view of a portion of the garment of FIG. 1 along side seam 20 in the vicinity of leg opening edge 26 which is partially inwardly folded at an intermediate stage of forming a gusset fold. The dotted-line 22, also shown in FIG. 1, denotes a fold line which provides an outer lateral edge of the gusset fold to be formed from both front panel 11 and back panel 12. A corresponding fold line is indicated by dotted line 24 in the rear panel. Fold line 24 correspondingly provides the other outer lateral edge of the gusset fold to be formed. Thus, the gusset is formed by inwardly folding the garment along fold lines 22, 24 and side seam 20, at its leg opening 26 at point A to point B along side seam 20. A gusset fold, e.g., a gathered and folded generally wedge- or triangular-shaped portion of the material of the garment is thus formed within the polygon defined by lines joining points AB (center fold line, along seam 20) and BD and BC (respective outer lateral edges 24, 22 of the gusset fold). As shown, the resulting gusset fold converges in a direction away from the leg edge 26 with the outer lateral edges 22, 24 of the gusset being drawn together as more fully shown in FIGS. 3 and 3A. Thus, the outer lateral edges 22, 24 of the gusset fold intersect one another at an angle subtending a portion 26a of the leg opening edge 26, with the subtended portion (the edge portion DAC in FIG. 2) being bisected by a center fold line AB of the gusset, along a section of seam 20. The router lateral edges 22, 24 and the fold line AB together with the subtended edge portion DAC define opposed congruent triangular faces of material, viz, the triangular faces ABC and ABD.

The center fold line AB in the FIGS. 1–3A embodiment, is reinforced against tearing by the side seam 20. However, it is within the purview of the present invention to utilize the gusset fold in the side portion of a panty-type garment or otherwise in a garment at an opening thereof, wherein the gusset center fold line is not reinforced. That is, the center fold line need not coincide with a seam or other reinforcement. Preferably however, the center fold line of the gusset is reinforced conveniently by seam 20 as shown in FIGS. 1–3A, particularly when the garment is constructed of low basis weight material, such as the low basis weight materials used in disposable garments. The reinforcement along center fold line need not of course be a seam of the garment but may be provided by any suitable means such as by reinforcing strips, or the like.

Figure 3:
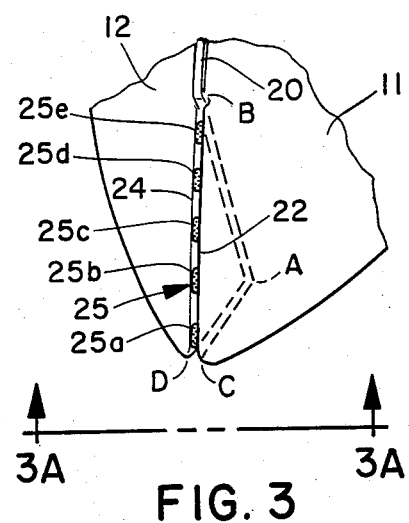
FIG. 3 is a perspective view of a portion of the side seam of the garment of FIG. 1, showing an inwardly-folded gusset fold in accordance with one embodiment of the invention formed therein.
Figure 3A:
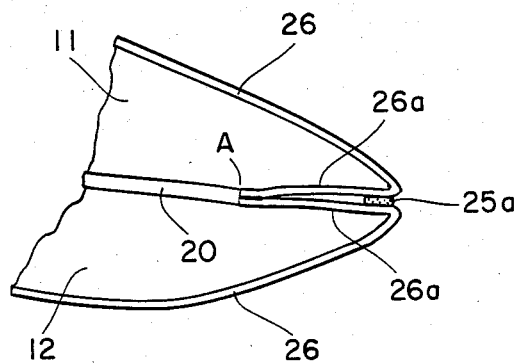
FIG. 3A is a view taken along line 3A—3A of FIG. 3.

FIG. 3 is a perspective view corresponding to FIG. 2, but, together with FIG. 3A, showing the completed gusset fold wherein the outer lateral edges 22, 24 of the gusset have been brought together and disengagably bonded to one another, such as by a series of intermittent ultrasonic weld bonds 25a, 25b, 25c, 25d and 25e. Each of the weld bonds is at regularly spaced intervals along the length of the opposed outer lateral edges 22, 24 of the gusset fold. Intermittent bonding of outer lateral edges 22, 24 may be suitably carried out as by means of a slotted hot knife, pattern-applied adhesive or the like, or may be patterned ultrasonic bonding. In any case, the intermittent bonding will permit the resulting bonded outer lateral edges 22, 24 to be manually disengaged from one another, simply by pulling apart the intermittent bonded edges to expose a part at least of the interior of the gusset fold to a predetermined extent. Thus, the leg opening of the panty-type garment shown in FIGS. 1-3A may be manually adjusted to larger sizes simply by grasping between thumb and forefinger the material on either side of the intermittently bonded seam 22/24 and pulling the material apart to break one or more of bonds 25a, 25b, 25c, 25d and 25e, to open the gusset fold to a desired extent. It will be appreciated that due to the angled configuration of the lateral outer edges of the gusset (as shown best in FIG. 2), the intermittently bonded seam 22/24 may be pulled open a selected distance therealong to increase the leg opening dimension by a desired amount, with proportionally larger portions of the opened gusset seam 22/24 corresponding to proportionally larger leg openings for the garment. Thus, the construction shown is extremely simple and manually openable to provide a range of sizes and thereby a proper fit for the garment opening. In panty-type garments used for toilet training and control of incontinence, leg opening size is important because both comfort of the wearer and control of leakage through the leg opening must be accommodated. If all of the intermittent bonds are disengaged, the gusset fold can be opened completely and will revert generally to the condition illustrated in FIG. 2, but with segments 26a opened outwardly to be aligned as a straight-line or smooth curve segment of leg opening 26.

While not shown or specifically described in connection with FIGS. 1-3A above, it will be appreciated that a similar gusset type construction may be utilized with the waist opening 36 of the garment to provide a range of varying waist sizes therefor.

Although the manually disengagable bonding of the outer lateral edges of the gusset has been shown as being effected by intermittent bonds 25a-25e, it will be appreciated that other methods of bonding or joining the outer seam of the gusset may be utilized to the same effect. For instance, it may be possible to provide a continuous bond of sufficiently low bond strength between the opposed faces of the gusset so as to be manually disengagable; a low tack, high shear strength adhesive may be useful for such bonding of the opposed gusset surfaces. Further, spot welding of the entire surface of the opposed gusset faces, i.e., the triangular faces ABC and ABD, may be usefully employed in some instances. It will therefore be appreciated that various approaches may be usefully employed to secure the gusset fold and its outer lateral edges in manually disengagable bonded character, and all such suitable means and methods are to be regarded as being within the scope of the present invention.

Figure 3B:
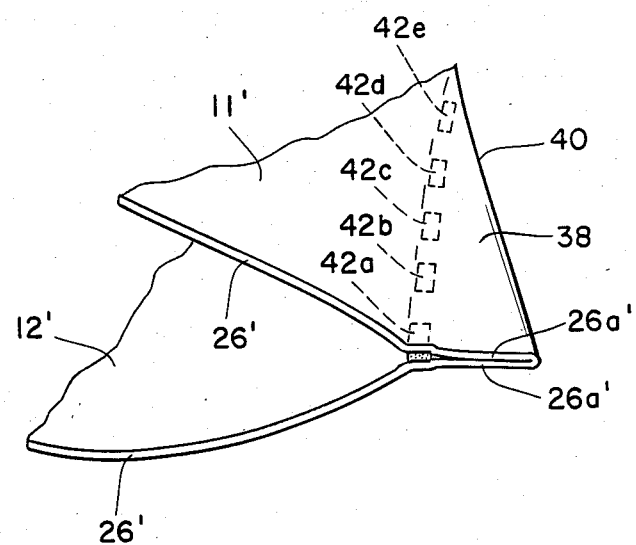
FIG. 3B is a perspective view similar to the end view of FIG. 3A but showing an outwardly-folded gusset fold in accordance with another embodiment of the invention.

The completed gusset fold illustrated by FIGS. 3 and 3A is an inwardly folded gusset fold which extends inwardly of the leg opening. FIG. 3B illustrates an alternate embodiment of the invention wherein the gusset fold 37 is obtained by folding together the inner-facing surfaces of the garment to provide a gusset fold 37 disposed exteriorly of the garment having an outer fold 40 with disengagable intermittent bonds 42a, 42b, 42c, 42d and 42e shown in dotted outline in FIG. 3B as sandwiched between and joining an inner lateral seam (unnumbered) of gusset fold 38. The intermittent bonds 42a-42e may comprise intermittent ultrasonic weld bonds spaced apart one from the other at intervals along the length of the inner lateral seam of the gusset fold. The garment in which the gusset fold 38 is formed may have a side seam corresponding to side seam 20 of the garment of FIG. 3A, which side seam may, but need not, coincide with outer fold 40 illustrated in FIG. 3B. The garment of FIG. 3B may thus be comprised of a front panel 11' joined to a rear panel 12', along a side seam (not illustrated in FIG. 3B) which would coincide with outer fold 40. Gusset fold 38 subtends a portion 26a' of the leg opening edge 26'. As with the FIG. 3A embodiment, if it is desired to enlarge the size of the leg openings, it is necessary only to grip the material adjacent the leg opening on either side of the gusset fold between respective thumbs and forefingers and pull apart the material to successively break or disengage one or more of intermittent bonds 42a, 42b, etc. In this manner, the size of the leg opening may be increased a selected amount.

While, as noted above, the intermittent bonds may be provided by any suitable means such as adhesive, or ultrasonic or thermal welding a preferred form of construction is the utilization of "thermal bonding" which term, as used herein and in the claims, is intended to include ultrasonic welding or bonding as well as the use of high temperature knives or dies. Thermal bonding is a preferred mode of applying the intermittent bond because the thermal bonding will weaken the fusible, i.e., thermally bondable, material immediately adjacent the bond point. This facilitates disengaging the intermittent bonds by avoiding the need to separate the two bonded surfaces while leaving the material intact. Instead, a portion of the weakened material adjacent the bond area on one of the faces of the gusset will tear away so that as the gusset fold is opened the bond itself remains intact but is separated from one of the gusset faces by the tearing of the immediately adjacent material. For example, with reference to FIGS. 2 and 3, when a disengagable ultrasonic weld bond, say 25a, is disengaged the bond will usually stay intact and remain at one of lateral edges 22 or 24 and separate from the other with a small tear resulting in the fabric along the edge from which the bond is removed. As more of the intermittent bonds 25b, etc., are disengaged, the bonds themselves will remain either along lateral edges 22 or 24 with a small tear resulting along the fold from which they are removed. Given the disposable nature of the garment, which may have a somewhat fuzzy or soft nap on its outer surface, the small tears do not present a significant problem of appearance or unduly adversely effect structural integrity. This tear-away aspect is advantageous because it avoids the necessity for utilizing a material of construction with a tear strength greater than the separation strength of the bond, and avoids the necessity of having to accurately control the bond strength to a level below the tear strength of the material. Such low bond strength may be insufficient to keep the gusset fold intact. The tear-away feature thus makes advantageous use of the inherent weakening of a material, such as a nonwoven fabric or thermoplastic film material in the area immediately adjacent a thermal bond, e.g., an ultrasonic bond. From the foregoing, it will be clear that as used herein and in the claims, the term "disengagably bonded" or the like, with reference to the bonds of the invention, does not necessarily require that the two bonded together layers of material be separated at the bond site itself, but includes tearing away of a portion of the material of one of the bonded layers adjacent the bond site, so as to permit unfolding of the gusset fold.

Accordingly, preferred materials of construction are those which are thermally bondable, preferably by ultrasonic bonding, and which are weakened in the area immediately adjacent the thermal bond so that at least one of the bonded together layers will tear or fail, but only in the weakened area immediately adjacent the bond site, in order to permit unfolding of the gusset fold. Accordingly, preferred thermoplastic films include by way of example and not limitation, polymers of polypropylene, ethylene ethylene-methyl-acrylate, ethylene-vinyl-acetate, ethylene-ethyl-acrylate, and blends, copolymers or co-extrusions of two or more of the foregoing. Preferred nonwoven materials include, by way of example and not limitation, thermally bonded polypropylene staple fiber or spunbonded polypropylene, or other nonwovens such as thermally bonded polyester, or blends of polypropylene, polyester, or blends of polypropylene, polyester, cotton, rayon, chisso, and the like. Composite layers of thermoplastic film and nonwoven materials are preferably selected from film-coated nonwovens wherein the nonwoven material is extrusion- or otherwise coated with any suitable thermoplastic film, e.g., polypropylene, ethylene-methyl-acrylate, poly-ethylene-vinyl-acetate, ethyleneacrylic-acid, or a blend of two or more of the aforementioned polymers.

While specific preferred embodiments of the present invention have been shown and described in detail, it will be appreciated that numerous modifications and variations thereof are possible, together with other embodiments, and accordingly, all such apparent modifications, variants, and embodiments are to be regarded as being within the spirit and the scope of the present invention.

What is claimed is:

1. A garment including at least one opening for encircling a portion of a wearer's body and having at the periphery of the opening a gusset fold comprised of disengagably bonded together gusset faces, whereby the opening can be increased in size by manual disengagement of at least a portion of the bonded together gusset faces.

2. The garment of claim 1 wherein the bonded together faces of the gusset fold are inwardly-folded sections of an outer-facing surface of the garment and define a lateral gusset seam in said outer-facing surface.

3. The garment of claim 2 wherein the gusset faces are disengagably bonded together along the lateral gusset seam.

4. The garment of claim 3 wherein the gusset faces are intermittently disengagably bonded together.

5. The garment of claim 1 wherein the gusset fold is intermittently disengagably bonded.

6. The garment of claim 1 wherein the bonded together faces of the gusset fold are sections of an inner-facing surface of the garment, whereby the gusset fold is disposed exteriorly of the opening.

7. The garment of claim 1 wherein the gusset fold is folded along a center fold line and comprises two disengagably bonded together faces.

8. The garment of claim 7 wherein the center fold line coincides with a seam of the garment.

9. The garment of claim 7 wherein the center fold line is reinforced against tearing.

10. The garment of claim 1 wherein the gusset faces are intermittently disengagably bonded together.

11. A panty-type garment having leg openings and including one or more gusset folds at the leg openings, the gusset folds comprising gusset faces being manually disengagably bonded to one another, whereby the leg openings may be adjusted in use to larger sized legs by manual disengagement of at least a portion of the bonded gusset faces.

12. The garment of claim 1 or claim 11 wherein at least the gusset fold of the garment comprises a thermally bondable material and the gusset faces are thermally disengagably bonded together.

13. The garment of claim 12 wherein the gusset faces are ultrasonically disengagably bonded together.

14. The garment of claim 12 wherein the thermally bondable material is weakened in the area immediately adjacent the disengagably bonded areas to facilitate disengagement of the bonded together gusset faces by mechanical failure of the material in the weakened area.

15. The garment of claim 14 wherein the gusset faces are ultrasonically disengagably bonded together.

16. The garment of claim 15 wherein the gusset faces are intermittently bonded together.

17. The garment of claim 15 wherein at least the gusset fold of the garment comprises a thermoplastic material.

18. A method for making a garment having adjustable openings therein for encircling a portion of a wearer's body, comprising the steps of:
    providing a garment having one or more of said openings therein;
    folding material at said opening to form therein gusset faces providing one or more gusset folds at the edge of said leg openings; and
    manually disengagably-bonding the gusset faces of a gusset fold to one another.

19. The method of claim 18 including angularly inwardly folding material at said opening to form said gusset faces.

20. The method of claim 18 including intermittently bonding faces of the gusset folds to one another.

21. The method of claim 18 including forming a gusset seam by the aforesaid folding and intermittently bonding the gusset faces at the gusset seam.

22. The method of claim 18 wherein the garment has an inner-facing surface and an outer-facing surface and including forming the gusset fold by inwardly folding sections of the outer-facing surface.

23. The method of claim 18 wherein the garment has an inner-facing surface and an outer-facing surface and including forming the gusset fold by folding together of the inner-facing surface to provide a gusset fold disposed exteriorly of the garment.

24. The method of claim 23 including folding the gusset fold to have a center fold line along at least a portion of the side seams adjacent the leg openings.

25. The method of claim 18 wherein at least the gusset fold of the garment comprises a thermally bondable material and including thermally bonding the faces of the gusset folds to one another.

26. The method of claim 25 wherein the thermally bondable material is weakened in the area immediately adjacent the bonding sites.

* * * * *